US009931072B2

(12) United States Patent
Roig et al.

(10) Patent No.: US 9,931,072 B2
(45) Date of Patent: *Apr. 3, 2018

(54) METHOD FOR CHARACTERIZING A SAMPLE BY MEASUREMENT OF A BACKSCATTERED OPTICAL SIGNAL

(71) Applicant: Commissariat a L'Energie Atomique et aux Energies Alternatives, Paris (FR)

(72) Inventors: Blandine Roig, Guemene sur Scorff (FR); Anne Koenig, Saint Martin d'Uriage (FR); Jean-Marc Dinten, Lyons (FR); Francois Perraut, Saint Joseph de Riviere (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/015,306

(22) Filed: Feb. 4, 2016

(65) Prior Publication Data
US 2016/0228047 A1 Aug. 11, 2016

(30) Foreign Application Priority Data

Feb. 6, 2015 (FR) ...................... 15 50982

(51) Int. Cl.
*G01J 3/44* (2006.01)
*G01N 21/65* (2006.01)
(Continued)

(52) U.S. Cl.
CPC ............ *A61B 5/441* (2013.01); *A61B 5/0059* (2013.01); *A61B 5/7278* (2013.01);
(Continued)

(58) Field of Classification Search
CPC ........................... G01N 21/65; G01N 21/6486
(Continued)

(56) References Cited

U.S. PATENT DOCUMENTS

2003/0191398 A1 10/2003 Motz et al.
2004/0073120 A1 4/2004 Motz et al.
(Continued)

FOREIGN PATENT DOCUMENTS

EP 2 762 064 A2 8/2014
WO WO 2011/115627 A1 9/2011

OTHER PUBLICATIONS

French Preliminary Search Report dated Dec. 16, 2015 in French Application 15 50982, filed Feb. 6, 2015 (with English Translation of Categories of Cited Documents and Written Opinion).

*Primary Examiner* — Carl H Layno
*Assistant Examiner* — Jon Eric C Morales
(74) *Attorney, Agent, or Firm* — Oblon, McClelland, Maier & Neustadt, L.L.P.

(57) ABSTRACT

Determining an optical property of a sample having an illumination of a surface of the sample with the aid of a light beam, so as to form, on the surface of the said sample, an elementary illumination zone, corresponding to the part of the said surface illuminated by the said sample. A detection of N optical signals, backscattered by the sample, each optical signal emanating from the surface of the sample at a distance, termed the backscattering distance, from the said elementary illumination zone, N being an integer greater than or equal to 1, so as to form as many detected signals. A determination of at least one optical property of the sample, by comparison between: a function of each signal thus detected and a plurality of estimations of the said function each estimation being carried out by considering a predetermined value of the said optical property, characterized in that during the said detection step, at least one backscattering distance is less than 200 pm.

10 Claims, 6 Drawing Sheets

(51) Int. Cl.
*A61B 5/00* (2006.01)
*G01N 21/47* (2006.01)
*G01N 21/49* (2006.01)

(52) U.S. Cl.
CPC ....... *G01N 21/474* (2013.01); *G01N 21/4795* (2013.01); *G01N 21/49* (2013.01); *A61B 2503/40* (2013.01)

(58) Field of Classification Search
USPC .......................................................... 600/476
See application file for complete search history.

(56) References Cited

U.S. PATENT DOCUMENTS

| | | |
|---|---|---|
| 2012/0302892 A1 | 11/2012 | Lue et al. |
| 2013/0128264 A1 | 5/2013 | Wax et al. |
| 2014/0241994 A1 | 8/2014 | Koenig |
| 2016/0231249 A1* | 8/2016 | Roig .................. G01N 21/6486 |

* cited by examiner

METHOD FOR CHARACTERIZING A SAMPLE BY MEASUREMENT OF A BACKSCATTERED OPTICAL SIGNAL

TECHNICAL FIELD

The invention lies in the field of the characterization of samples, and especially biological samples, and more particularly the skin.

DESCRIPTION OF THE PRIOR ART

Optical measurements making it possible to characterize samples are widespread. This entails, in particular, characterizing the optical properties or the nature of the materials of which a sample is composed. Measurements based on the detection of a signal backscattered by a sample illuminated by a light beam may be cited in particular. These entail, in particular, Raman spectrometry, fluorescence imaging or diffuse reflectance spectrometry.

Diffuse reflectance spectrometry, often designated by the acronym DRS, consists in utilizing the light backscattered by a scattering object subjected to an illumination, generally pointlike. This technique turns out to be efficacious for characterizing optical properties of objects, in particular the scattering or absorption properties.

Implemented on the skin, this technique makes it possible for example to characterize the dermis, as described in document EP 2762064. The authors of this document describe a measurement probe intended to be applied against the skin. This probe comprises a central optical fibre, termed the excitation fibre, intended to direct a light beam towards a skin sample. Optical fibres, termed detection fibres, disposed around the central fibre, gather an optical signal backscattered by the dermis. Means of spectral analysis of the optical signal thus collected, which are coupled with calculation algorithms, make it possible to estimate parameters of the dermis, in particular the concentration of certain chromophores, for example oxyhaemoglobin or deoxyhaemoglobin, and also parameters governing the journey of the photons in the dermis, especially the reduced scattering coefficient $\mu s'$ as well as the absorption coefficient $\mu a$.

According to the principles of the scattering of the light in a scattering medium, the bigger the separation between the excitation fibre and a detection fibre, the more the light gathered by the detection fibre is dependent on the optical properties in the deep layers of the dermis, that is to say beyond a depth interval lying between 300 μm and a few mm. Stated otherwise, the more the distance between the excitation fibre and the detection fibre increases, the more the result is representative of the optical properties of the deep layers of the medium examined. Conversely, the more this distance decreases, the more the result is representative of the surface layers of the scattering medium.

Now, in order to perform a sufficiently sensitive measurement, each fibre has a diameter equal to a few hundreds of microns, typically 500 μm for the excitation fibre and 300 μm for each detection fibre. Moreover, on account of fabrication constraints, it is hardly conceivable to significantly reduce the distance between these fibres. It follows from this that the minimum separation between each fibre cannot be less than a threshold value, greater than 400 μm, and usually millimetric.

Therefore, whereas the method and the device described in this publication are suitable for the characterization of the dermis, they are not able to characterize the epidermis, the latter extending, depending on the individual and the body zone, over the first ten or so micrometers of the skin.

The invention is aimed at solving this problem, by proposing a measurement method and a device which are able to determine the optical properties of the epidermis and, in a more general manner, the optical properties of the surface layer of a scattering medium.

DESCRIPTION OF THE INVENTION

Thus, a subject of the invention is a method for determining an optical property of a sample, comprising the following steps:
illuminating a surface of the sample with the aid of a light beam, so as to form, on the surface of the said sample, an elementary illumination zone, corresponding to the part of the said surface illuminated on the said sample;
detecting N optical signals, backscattered by the sample, each optical signal emanating from the surface of the sample, at a distance, so-called backscattering distance, of the said elementary illumination zone, so as to form as many detected signals, N being an integer greater than or equal to 1, each elementary detection zone being separated from the said elementary illumination zone;
determining at least one optical property of the sample, by comparison between a function of each signal thus detected and a plurality of estimations of the said function, each estimation being carried out by considering a predetermined value of the said optical property, wherein
during the said detection step, at least one backscattering distance, separating an elementary zone for detecting the said elementary illlumination zone, is less than 200 μm.

Thus, each elementary detection zone is distinct from the elementary illumination zone and does not overlay on the latter. It is separated from the latter by a non-zero distance.

Preferably, at least one backscattering distance can be less than 150 μm.

Preferably, at least two backscattering distance are less than 200 μm.

The said optical property can be chosen from among
a scattering anisotropy factor, representing a mean angle of scattering;
an absorption coefficient;
a scattering coefficient;
a reduced scattering coefficient.

The method can also comprise:
detecting at least two backscattered optical signals emanating from the surface of the sample:
  a near backscattered signal, emitted at a so-called near backscattering distance, less than 200 μm;
  a far backscattered signal, emitted at a so-called far backscattering distance, greater than the said near backscattering distance;
determining a first optical property on the basis of the said near backscattered signal;
determining a second optical property, different from the first optical property, on the basis of the said far backscattered signal.

It can also comprise:
detecting at least two near backscattered optical signals, emanating from the surface of the sample at two different backscattering distances, these two distances being less than 200 μm, determining a reduced scattering coefficient from the said far optical signal, determining a the scattering coefficient and the scattering anisotropy factor from the two near backscattered optical signals, as well as of the previously determined reduced scattering coefficient.

It can further comprise:

detecting at least two far backscattered optical signals, emanating from the surface of the sample at two different backscattering distances, the two backscattering distances being greater than 200 μm, determining the absorption coefficient from the said far backscattered optical signals.

The sample examined can be the skin of a human or of an animal.

The backscattered optical signal can be measured at a plurality of wavelengths.

According to one embodiment, the said function of the signal is the reflectance, representing the intensity of the detected signal, corresponding to the said backscattering distance, relative to the intensity of the said light beam.

DETAILED DESCRIPTION

Figure 1:
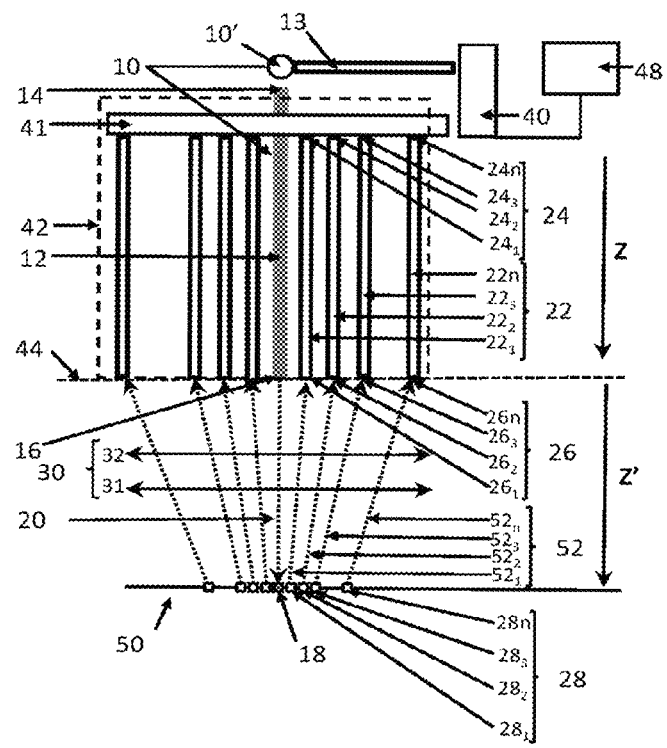
FIGS. 1 and 2 represent a first embodiment of a device according to the invention.

FIG. 1 represents a first embodiment of a device according to the invention. It comprises a light source 10, which comprises in this first example a white light source 10'.

The light source 10 comprises, in this first embodiment, an illumination optical fibre 12, extending between a proximal end 14 and a distal end 16. The illumination optical fibre 12 is able to collect the light, through a proximal end 14 and to emit a light beam 20 towards the sample through a distal end 16, the said light beam then being directed towards the surface of a sample 50. In such a configuration, the light source 10 is termed fibred.

The diameter of the emission optical fibre 12 is between 100 μm and 1 mm, and is for example equal to 400 μm.

By point source is meant a source whose area is less than 1 cm², and preferably less than 5 mm², and more preferably less than 1 mm².

The device also comprises a plurality of detection optical fibres $22_1$, $22_2$, $22_3$ ... $22_n$, the index n lying between 1 and N, N designating the number of detection optical fibres in the device. N is a natural integer generally lying between 1 and 100, and preferentially lying between 5 and 50. Each detection fibre $22_1$, $22_2$, $22_3$ ... $22_n$ extends between a proximal end $24_1$, $24_2$, $24_3$ ... $24_n$ and a distal end $26_1$, $26_2$, $26_3$ ... $26_n$.

In FIG. 1, the references 22, 24 and 26 designate respectively the set of detection fibres, the set of proximal ends of the detection fibres and the set of distal ends of the detection fibres.

The diameter of each detection optical fibre 22 is between 50 μm and 1 mm, and is for example equal to 300 μm.

The proximal end 24 of each detection optical fibre 22 is able to be optically coupled to a photodetector 40.

The distal end $26_1$, $26_2$, $26_3$ ... $26_n$ of each detection optical fibre 22 is able to collect respectively an optical signal $52_1$, $52_2$, $52_3$ ... $52_n$ backscattered by the sample 50, when the latter is exposed to the light beam 20.

The photodetector 40 is able to detect each optical signal $52_1$, $52_2$, $52_3$ ... $52_n$ so as to form a detected signal ($S_1$, $S_2$, $S_3$, ... $S_n$) respectively representative of each detected optical signal.

It may be a spectrophotometer, able to establish the wavelength spectrum of the optical signal collected by the detection optical fibre 22 to which it is coupled.

The photodetector is able to be connected to a microprocessor 48, the latter being configured to implement the methods described hereinafter.

The detection optical fibres 22 extend parallel to one another, parallel to a longitudinal axis around the emission optical fibre 12. They are held fixed with respect to one another by a holding element 42. Their distal ends 26 are coplanar, and define a detection plane 44.

Figure 2:
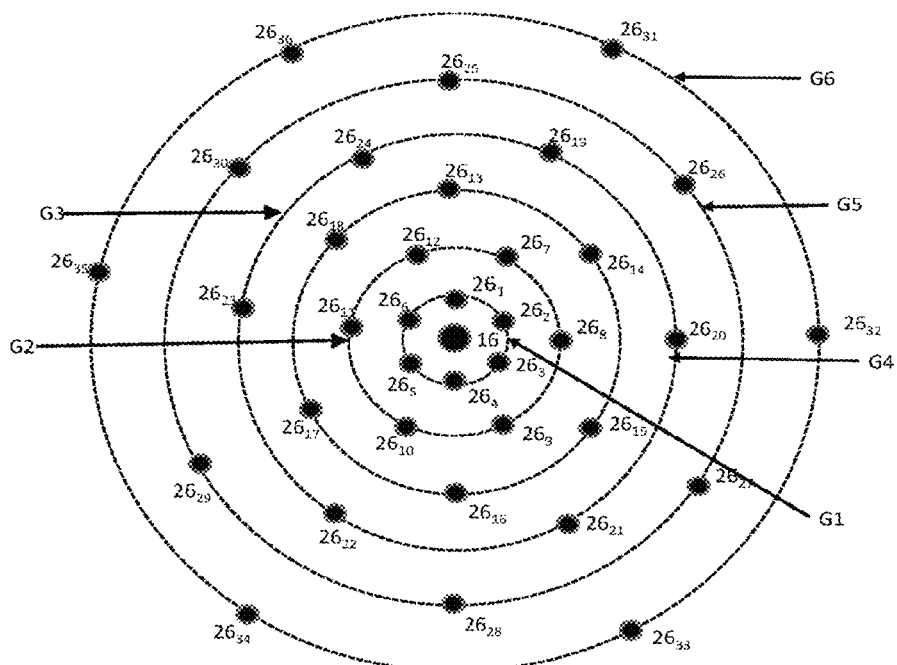

FIG. 2 represents a sectional view of the device, in the detection plane, formed by the set of distal ends 26 of the N detection fibres. In this example, N is equal to 36. As may be seen, the detection optical fibres are distributed according to:

a first group $G_1$ of six detection optical fibres $22_1$ ... $22_6$, disposed regularly along a circle centred on the emission optical fibre 12, in such a way that the distal end $26_1$ ... $26_6$ of each fibre of this group is a first distance $d_1$ equal to 300 μm away from the distal end 16 of the emission optical fibre 12.

a second group $G_2$ of six detection optical fibres $22_7$ ... $22_{12}$, disposed regularly along a circle centred on the emission optical fibre 12, in such a way that the distal end $26_7$ ... $26_{12}$ of each fibre of this group is a second distance $d_2$ equal to 700 μm away from the distal end 16 of the emission optical fibre 12.

a third group $G_3$ of six detection optical fibres $22_{13}$ ... $22_{18}$, disposed regularly along a circle centred on the emission optical fibre 12, in such a way that the distal end $26_{13}$ ... $26_{18}$ of each fibre of this group is a third distance $d_3$ equal to 1.1 mm away from the distal end 16 of the emission optical fibre 12.

a fourth group $G_4$ of six detection optical fibres $22_{19}$ ... $22_{24}$, disposed regularly along a circle centred on the emission optical fibre 12, in such a way that the distal end $26_{19}$ ... $26_{24}$ of each fibre of this group is a fourth distance $d_4$ equal to 1.5 mm away from the distal end 16 of the emission optical fibre 12.

a fifth group $G_5$ of six detection optical fibres $22_{25}$ ... $22_{30}$, disposed regularly along a circle centred on the emission optical fibre 12, in such a way that the distal end $26_{25}$ ... $26_{30}$ of each fibre of this group is a fifth distance $d_5$ equal to 2 mm away from the distal end 16 of the emission optical fibre 12.

a sixth group $G_6$ of six detection optical fibres $22_{31}$ ... $22_{36}$, disposed regularly along a circle centred on the emission optical fibre 12, in such a way that the distal end $26_{31}$ ... $26_{36}$ of each fibre of this group is a sixth distance $d_6$ equal to 2.5 μm away from the distal end 16 of the emission optical fibre 12.

When speaking of a distance between two fibres, or between a fibre or a light beam, a centre to centre distance is meant.

Thus, each distal end $26_n$ of a detection optical fibre $22_n$ is placed, in a plane perpendicular to the longitudinal axis Z according to which these fibres extend, at a distance $d_n$ from the light source 10 (that is to say from the distal end 16 of the emission fibre 12), and, consequently, at a distance $d_n$ from the light beam 20 directed towards the sample 50.

The device can comprise a photodetector 40, able to be coupled to the proximal end $24_n$ of each detection optical fibre $22_n$. In this example, the photodetector is a spectrophotometer, able to determine the spectrum of an optical signal $52_1$ ... $52_n$ backscattered by the sample when the latter is exposed to the light beam 20. Accordingly, the proximal ends 24 of each group of detection optical fibres, described hereinabove, are grouped together and are, group by group, successively coupled to the photodetector 40 by means of an optical switch 41. Thus, the photodetector makes it possible to measure the spectrum of a radiation backscattered by the sample, under the effect of an illumination by the light beam 20.

The device can comprise a so-called excitation return optical fibre 13, a proximal end of which is coupled to the light source 10 and a distal end of which is able to be coupled to the photodetector 40. The use of this optical fibre is detailed at the end of the description.

The device also comprises an optical system 30, exhibiting a magnification factor G and an optical axis Z'. The magnification factor is preferably greater than 2, and more preferably greated than 5 or 10. In this example, the optical axis Z' coincides with the longitudinal axis Z according to which the detection optical fibres extend, thereby constituting a preferred configuration. In this example, the optical system 30 comprises:

- a microscope objective 31, placed in infinite focus configuration, able to produce an image at infinity of the surface of the observed sample, when the latter is placed at the focus of this objective. In this example, it is a Zeiss brand objective, reference 200X Plan Aprochromat, with numerical aperture 0.8 and focal length $f_1$=8.25 mm;
- an achromat doublet 32, of focal length $f_2$=50 mm, adjoined to the objective 31, able to project the image provided by the latter into the detection plane 44, this plane being placed at a distance equal to the focal length of the doublet.

The optical system 30 described hereinabove exhibits a magnification factor G equal to the ratio of the focal lengths, i.e. G≈6.

Preferably, the optical system 30 is removable and interchangeable, thereby allowing, by using the same device, the use of optical systems exhibiting different magnification factors.

In a general manner, the optical system 30 makes it possible to form an image of the surface of the sample 50 on the detection plane 44 formed by the distal ends 26 of each detection optical fibre 22, with a given magnification factor G. Thus, each distal end $26_1$, $26_2$ ... $26_n$ is respectively conjugated with an elementary detection zone $28_1$, $28_2$ ... $28_n$ of the surface of the sample. In this manner, each detection optical fibre $22_1$, $22_2$, ... $22_n$ is able to collect respectively an elementary optical signal $52_1$, $52_2$, ... $52_n$ backscattered by the sample, each elementary optical signal $52_1$, $52_2$, ... $52_n$ emanating from the elementary detection zone $28_1$, $28_2$ ... $28_n$.

Thus, each of the said distal ends $26_1$, $26_2$ ... $26_n$ can be situated in an image focal plane of the optical system 30, and conjugated with an elementary detection zone $28_1$, $28_2$ ... $28_n$ situated in the object focal plane of the said optical system, on the surface of the sample.

Likewise, the distal end 16 of the emission fibre 12 is conjugated with an elementary illumination zone 18 on the surface of the sample, this elementary illumination zone constituting the point of impact of the light beam 20 on the surface of the sample 50.

In a general manner, and whatever the embodiment, the term elementary zone designates a part of the surface of the sample whose dimensions are sufficiently small to consider that it is traversed by a homogeneous luminous radiation. Stated otherwise, an elementary zone is a zone of delimited shape, preferably pointlike, that is to say whose diameter or diagonal is less than 5 mm, and preferably less than 1 mm, or indeed less than 500 μm.

An elementary illumination zone 18 is traversed by the light beam 20, propagating in the direction towards the sample 50, while an elementary detection zone 28*n* is traversed by a backscattered radiation (or optical signal) 52*n*, this radiation being produced by the backscattering, in the sample, of the light beam 20. The optical coupling, carried out by the optical system 30, allows each detection fibre 22*n* to collect the elementary backscattered radiation 52*n*, the latter corresponding to the backscattered radiation traversing the elementary zone 28*n*.

The holding element 42 can ensure a rigid link between the detection optical fibres 22 and the optical system 30, so as to hold the detection plane 44, formed by the distal ends 26 of the detection optical fibres at a fixed distance from the optical system 30.

Figure 3A:
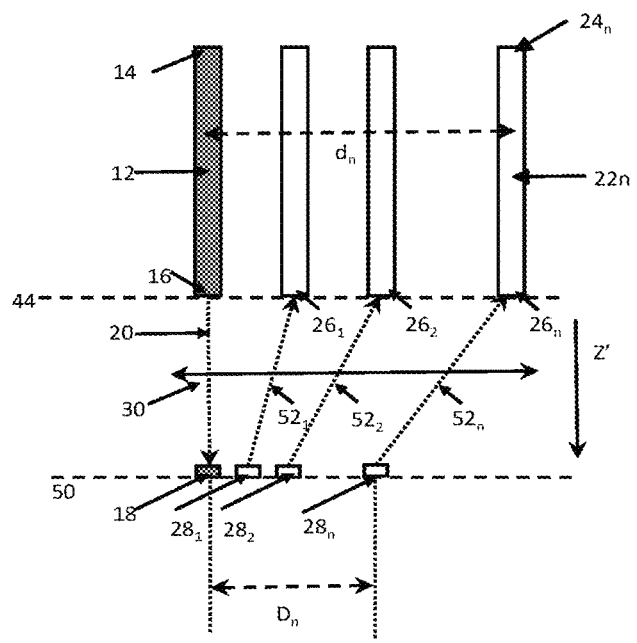
FIGS. 3A and 3B represent respectively a diagram of the device according to the prior art and according to the invention.

In relation to FIG. 3A, and this constitutes one of the essential points of the invention, if dn is the distance between the distal end 26*n* of a detection fibre 22*n* and the distal end 16 of the emission fibre 12, distance calculated in a plane perpendicular to the optical axis Z', the distance Dn between the elementary detection zone 28*n*, conjugate of the said distal end 26*n*, and the elementary illumination zone 18, conjugate of the said distal end 16, is such that:

$$Dn = \frac{dn}{G}$$

The distance $D_n$ is called the backscattering distance, since it corresponds to the distance, from the elementary illumination zone 18, at which the backscattered photons are emitted. This corresponds to the distance between the elementary illumination zone 18 and an elementary detection zone 28*n*.

Figure 3B:
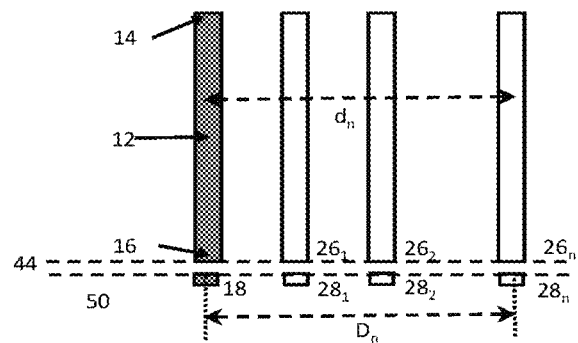

When its magnification factor is greater than 1, the optical system 30 tends to bring the elementary detection zones 28*n* significantly nearer to the elementary illumination zone 18 with respect to the prior art configuration, devoid of optical system, and represented in FIG. 3B in which the distal ends of each optical fibre (detection optical fibres and illumination optical fibre) are placed in contact with the surface of the sample. In the latter configuration, the backscattering distance Dn is equal to the distance dn between the respective distal ends of a detection optical fibre 22*n* and of the illumination optical fibre 12.

To summarize, in the prior art configuration, $D_n=d_n$, while by implementing the optical system 30, $$Dn = \frac{dn}{G}.$$

If the distance between the light beam and the distal end of a detection optical fibre is, upstream of the optical system, equal to a first distance, the backscattering distance is on the surface of the sample, equal to the said first distance weighted by the inverse of the said magnification factor.

The term "upstream" is understood by considering the direction of propagation of the light.

When the magnification factor is lower than 1, the elementary detection zones $28_n$ are further away from one another, and further away from the elementary illumination zone, their surface area being increased by the square of the magnification factor, with respect to the surface area of the distal end with which they are respectively associated. This makes it possible to perform a characterization of the sample with a lower spatial resolution, but over a higher depth than according to the prior art.

Figure 4:
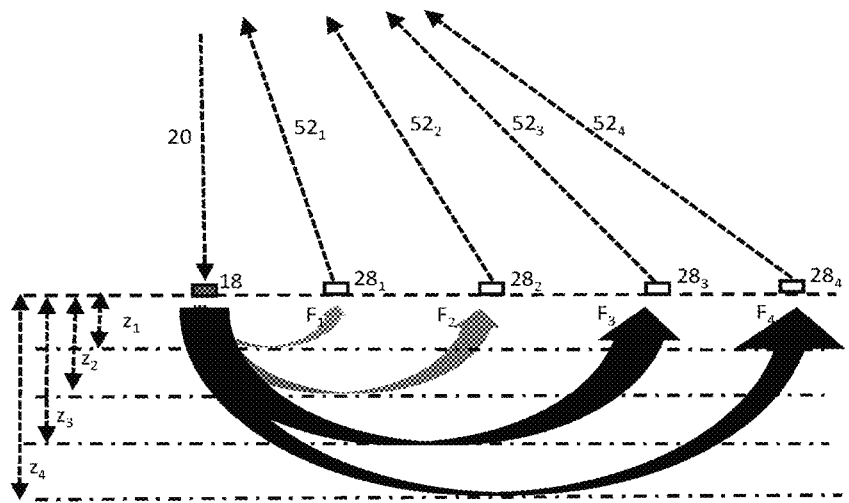
FIG. 4 is a diagram representing the propagation of light in a scattering sample as a function of the backscattering distance.

FIG. 4 summarizes this technical effect, each arrow $F_1$, $F_2$, $F_3$ and $F_4$ representing the path, in the sample 50, of the photons contributing to the respective backscattered signals $52_1$, $52_2$, $52_3$, $52_4$ respectively associated with the elementary detection zones $28_1$, $28_2$, $28_3$, $28_4$. The higher the separation between the elementary detection zones $28_1$, $28_2$, $28_3$, $28_4$ and the elementary illumination zone 18, the bigger the examined depth $z_1$, $z_2$, $z_3$, $z_4$ of the sample. Conversely, the smaller the separation between the elementary detection zones and the elementary illumination zone, the smaller the examined depth of the sample. This is achieved when the magnification factor is greater than 1.

More particularly, when the sample is skin, bringing the elementary detection zones nearer to the elementary illumination zone allows the characterization of the epidermis, which constitutes the surface layer of the skin, extending to a depth of between 100 and 300 μm, this not being conceivable with the prior art devices, whose spacing between each fibre is of the order of a few hundred micrometers or of a few millimeters.

Stated otherwise, the device according to the invention makes it possible to detect backscattering signals emitted by the sample at significantly smaller backscattering distances than according to the prior art, and this allows characterization of the optical properties of the surface layer of the observed sample.

When the photodetector is a spectrometer, the device makes it possible to perform measurements of the spectrum backscattered according to backscattering distances of a few tens to about 200 μm. One speaks of diffuse microreflectance spectroscopy, as opposed to diffuse reflectance spectroscopy, known from the prior art.

A method is now described which is capable of being implemented by the device described above, in order to estimate one or more optical properties of the sample examined, and more particularly of a surface layer of this sample, this layer extending in particular between the surface and a depth of less than $1/\mu_s'$.

In most biological tissues, and for the wavelengths of the visible or near-infrared spectrum, the reduced scattering coefficient is between 10 $cm^{-1}$ and 70 $cm^{-1}$. Hence, the method described hereinbelow is able to characterize a surface layer, extending between the surface of the sample and a depth of less than 1 mm, and more particularly less than 500 μm, or indeed 200 μm or 100 μm.

One of the envisaged applications is the characterization of the skin, which comprises three layers. The surface layer is the epidermis, whose thickness varies according to the individual and the part of the body, and is generally between a few tens of μm and 100 μm. The reduced scattering coefficient of the epidermis is between 50 and 70 $cm^{-1}$, according to wavelength. A value of 66 $cm^{-1}$ at the wavelength of 500 nm is for example cited in the literature.

The other two layers of the skin, deeper than the epidermis, and thicker than the latter are respectively the dermis, whose thickness varies between 1 and 2 mm, and then the hypodermis, whose thickness can exceed several mm.

The term optical property designates especially a factor governing the absorption and the scattering of photons in the scattering medium, in particular an absorption coefficient, a scattering coefficient, a reduced scattering coefficient, a scattering anisotropy coefficient.

Figures 5A, 5B, 5C:
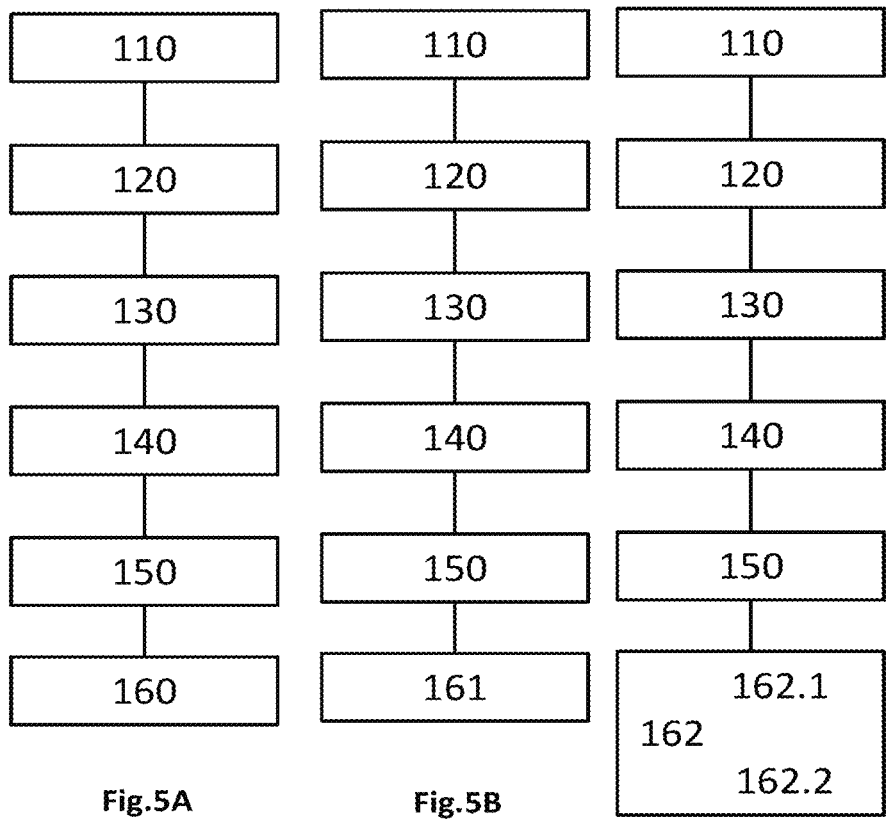
FIGS. 5A to 5C represent logic diagrams of 3 methods allowing the determination of at least one optical property of a sample.

In relation to FIG. 5A, the main steps of a method allowing the estimation of the optical scattering properties, in particular the absorption coefficient $\mu_a$ and the reduced scattering coefficient $\mu_s'$, are described. In this example, the magnification factor G rises to 6. As represented in FIG. 2, the device comprises 36 detection fibres, divided into 6 groups of 6 fibres, as a function of the distance $d_n$ separating each detection fibre $22_n$ from the illumination beam 50. These distances $d_n$ rise respectively to 300 μm; 700 μm; 1.1 mm; 1.5 mm; 2 mm; 2.5 mm.

By virtue of the optical system 30, each detection fibre $22_n$ is conjugated with an elementary detection zone $28_n$. The elementary detection zones are then themselves divided into 6 groups, as a function of the backscattering distance $D_n$ separating each elementary detection zone $28_n$ with the elementary illumination zone 18. Having regard to the magnification factor, the distances $D_n$ rise respectively to about 50 μm; 120 μm; 185 μm; 250 μm; 333 μm; 415 μm.

The following steps are then undertaken:

$1^{st}$ step 110: application of the device described above, facing the sample 50, in such a way that the examined surface is placed at the focus of the optical system 30.

$2^{nd}$ step 120: illumination of the sample by directing a light beam 20 against the surface of the sample, the part of the surface illuminated constituting the illuminated elementary zone 18.

$3^{rd}$ step 130: collection of an optical signal $52_1$, $52_2$, $52_3$, $52_4$ ... $52_n$ respectively backscattered by the sample, at the level of each elementary detection zone $28_1$, $28_2$, $28_3$, $28_4$ ... $28_n$, by the detection optical fibre $22_1$, $22_2$, $22_3$, $22_4$ ... $22_n$ whose distal end $26_1$, $26_2$, $26_3$, $26_4$ ... $26_n$ is respectively conjugated with the said elementary zone $28_1$, $28_2$, $28_3$, $28_4$ ... $28_n$.

$4^{th}$ step 140: measurement, with the aid of a photodetector 40, of the signal $S_n$ representative of the optical signal backscattered at each distance $D_n$ from the elementary illumination zone. The signal $S_n$ can in particular be established by aggregating the optical signals collected by the detection optical fibres of one and the same group. When the detector is a spectrometric detector, this constituting the preferred embodiment, it generates the spectrum of the signal $S_n$.

$5^{th}$ step 150: using each signal $S_n$ corresponding to a backscattering distance $D_n$, determination of a function $R_n$ called the reflectance of the signal, this reflectance being dependent on the signal $S_n$ and on calibration parameters. Thus, $R_n = f_{calib}(S_n)$, or $f_{calib}$ designates a calibration function, dependent on the instrumentation implemented, for example the effectiveness of collection by the fibres, the response function of the detector and the intensity of the incident light beam. The calibration function $f_{calib}$ can be obtained in the course of a calibration phase, previously or subsequent to the measurement on the sample.

For example, the reflectance $R_n$ can be obtained, from $S_n$, according to the expression:

$$R_n = f_{calib}(S_n) = \frac{S_n - S_{ref}}{S_{source}}$$

or according to the expression $$R_n = f_{calib}(S_n) = \frac{S_n - S_{ref}}{S_{source}} \times \frac{R_{std-n}}{S_{std-n}}$$

where:
- $S_n$ is the detected signal corresponding to the distance $D_n$ from the elementary illumination zone,
- $S_{ref}$ is a calibration signal, conveying the parasitic reflections of the optical system, obtained by activating the light source, but without the sample being present, the latter being for example replaced with an absorbent screen of black screen type.
- $S_{source}$ is the signal produced by the light source. $S_{source}$ can in particular be established by coupling the light source to the photodetector, for example by means of a so-called excitation return optical fibre 13, represented in FIG. 1.
- $S_{std-n}$ is a backscattering signal measured, by considering a backscattering distance $D_n$, on a phantom, whose optical properties (absorption, scattering) are known, by using the same device as that implemented to acquire the signal Sn.
- $R_{std-n}$ is an estimation of the reflectance produced, by the said phantom, at the backscattering distance $D_n$.

Other functions $f_{calib}$ establishing a relationship between the signal Sn measured by the photodetector and the reflectance Rn, especially by taking into account the parameters of the implemented instrumentation, are usable.

In a general manner, the reflectance represents the intensity of the backscattered signal. It is generally normalized by the intensity of the incident beam at the detector, in which case it represents a fraction of the backscattered incident beam.

$6^{th}$ step 160: for at least one wavelength $\lambda$, and by considering at least two backscattering distances $D_n$, determination of the pair $(\mu_a(\lambda), \mu'_s(\lambda))$ exhibiting the least disparity between the reflectance measured $R_n(\lambda)$, at the wavelength $\lambda$, and a reflectance $R_{n,\mu a,\mu s'}^{model}(\lambda)$ modelled for various values of $\mu_a(\lambda)$ and of $\mu'_s(\lambda)$, at a backscattering distance $D_n$. This determination can be carried out by minimizing a quadratic disparity, and for example according to the expression:

$$(\mu_a(\lambda), \mu'_s(\lambda)) = \operatorname{argmin}_{\mu_a(\lambda),\mu'_s(\lambda)} \left( \sum_{n=1}^{N} \left( R_{n,\mu a,\mu s'}^{model}(\lambda) - R_n(\lambda) \right)^2 \right)$$

where:
- N designates the number of distances taken into account
- $R_{n,\mu a,\mu s'}^{model}$ is a modelled reflectance function, established for the backscattering distance $D_n$, and for a pair of values $\mu_a$ and $\mu_s'$.

The various values of modelled reflectance $R_{n,\mu a,\mu s'}^{model}$ are obtained, for a plurality of pairs of values $\mu_a$, $\mu_s'$ in the course of a calibration phase, by numerical simulation, or experimentally, on phantom samples whose optical properties are known.

Figure 6:
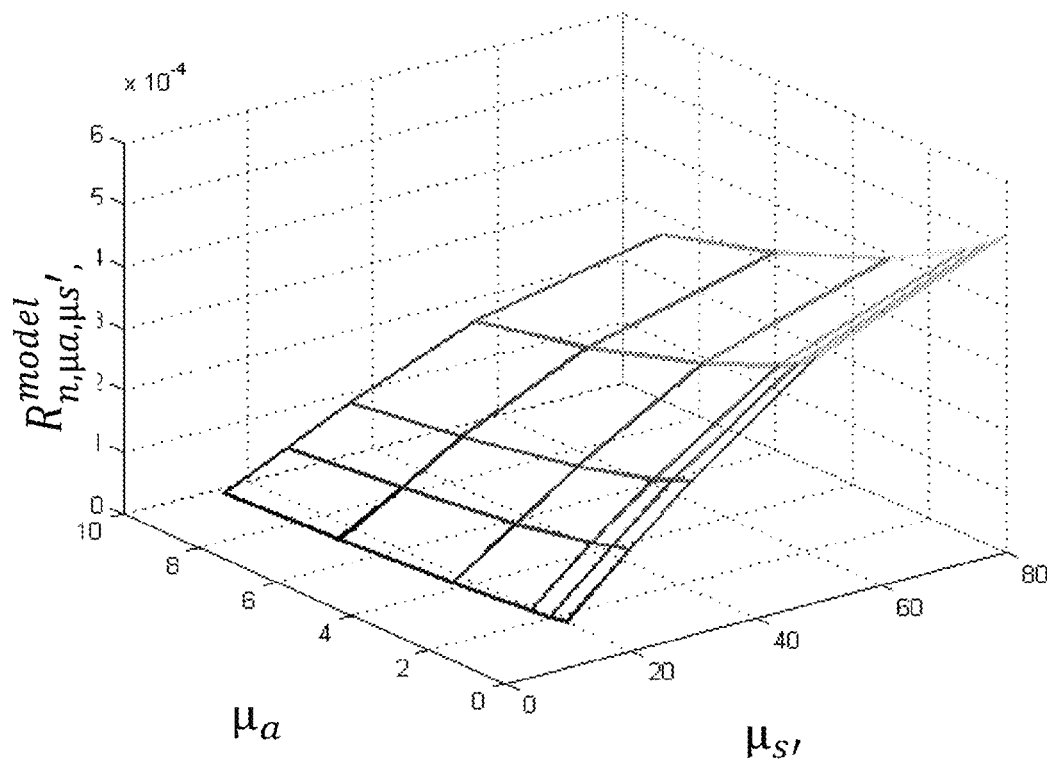
FIG. 6 represents a modelling of the reflectance, at a given backscattering distance, for various values of the absorption coefficient $\mu_a$ and of the reduced scattering coefficient $\mu_s'$.

For a given backscattering distance $D_n$ it is possible to represent a plurality of reflectances $R_{n,\mu a,\mu s'}^{model}$ modelled as a function of $\mu a$ and of $\mu s'$. FIG. 6 gives an exemplary representation of such modelled reflectances, by considering a backscattering distance equal to 400 µm and by taking into account values of the absorption coefficient lying between 0 and 10 cm$^{-1}$, and values of the reduced scattering coefficient lying between 0 and 100 cm$^{-1}$.

In a general manner, the notation $R_{n,p}^{model}$ designates a reflectance modelled at the backscattering distance $D_n$, taking into account predetermined values of at least one optical parameter p. The parameter p can correspond to an optical property, or a set of optical properties.

Steps 150 and 160 are implemented by the microprocessor 48, previously programmed for this purpose, and whose input data are the measurements carried out by the photodetector 40.

The inventors have noted that when the backscattering distance, separating an elementary illumination zone from an elementary detection zone, is less than 200 µm, or, more generally, less than a ratio $1/\mu s'$, the method described hereinabove makes it possible to characterize the optical properties of the surface layer of the sample examined, this surface layer extending between the surface of the sample and a depth of less than $1/\mu s'$.

FIGS. 7A to 7D, produced by the inventors, represent the value of the modelled reflectance $R_{n,\mu a,\mu s'}^{model}$ as a function of the coefficients $\mu a$, $\mu s'$, when considering a semi-infinite medium, and also by considering another optical parameter: the scattering anisotropy parameter, denoted g.

These simulations were carried out with a calculation code for Monte-Carlo type photon transport modelling. The backscattering distance is respectively equal to 65 µm for FIG. 7A, 120 µm for FIG. 7B, 185 µm for FIG. 7C and 415 µm for FIG. 7D. In each figure, four values of g were considered: 0.6; 0.7; 0.8; 0.9.

The scattering anisotropy factor, denoted g, represents the mean cosine of the scattering angle during scattering. This factor, dimensionless, is defined in the literature by the expression:

$$g = \int_{-1}^{1} f(\cos(\theta))\cos(\theta)d(\cos(\theta))$$

where
- $\theta$ represents the scattering angle,
- $f(\cos(\theta))$ is the probability associated with each value of the cosine of the scattering angle.

Perfectly anisotropic scattering, in which all the scattering angles would be equiprobable, is conveyed by an anisotropy coefficient equal to 0. Conversely, in the absence of scattering, the photons are not deviated and the anisotropy coefficient is equal to 1. The propagation of light in the medium is then governed solely by the absorption coefficient.

In biological media, it is admitted that scattering is anisotropic, favouring low scattering angles. One speaks of forward scattering. The anisotropy factor is chosen in an arbitrary manner, and generally between 0.8 and 0.95. This factor is then used as correction factor applied to the scattering coefficient $\mu_s$, as to establish a so-called reduced scattering coefficient, $\mu s'$, such that:

$$\mu_s' = \mu_s(1-g)$$

$\mu_s'$ is a reduced scattering coefficient, taking into account the anisotropic nature of the scattering in the scattering medium.

Figure 7A:
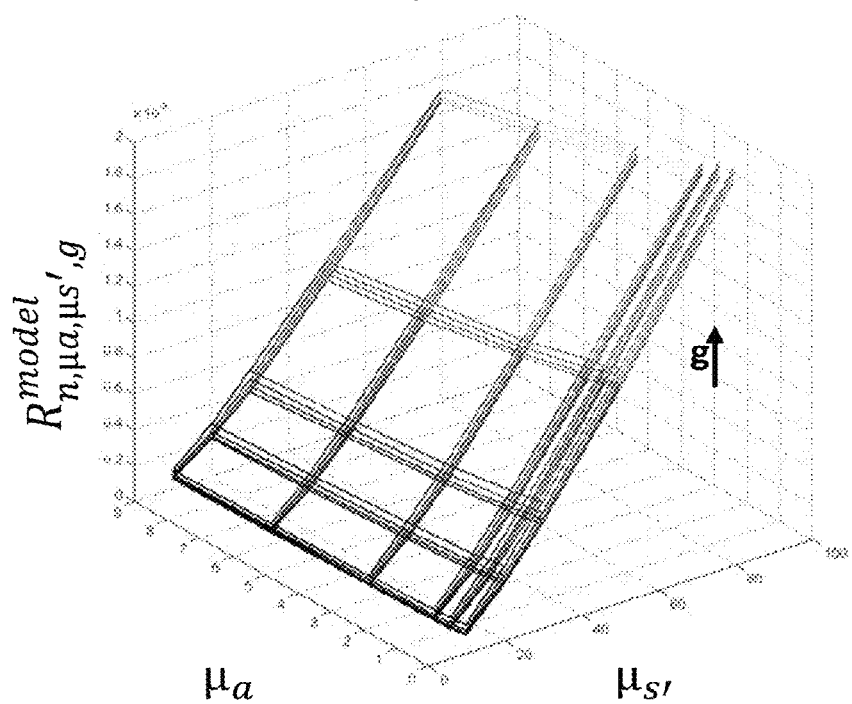
FIGS. 7A, 7B, 7C and 7D represent a modelling of the reflectance, for four respective backscattering distances, the reflectance being estimated for various pairs of values of the absorption coefficient $\mu_a$, of the reduced scattering coefficient $\mu_s'$ and of the scattering anisotropy coefficient g.

In FIG. 7A, it is possible to observe several substantially mutually parallel sheets, each sheet corresponding to a value of the scattering anisotropy coefficient g. The differences between the various sheets dwindle gradually in FIGS. 7B and 7C, and become negligible in FIG. 7D, in which is observed just a single sheet, which corresponds to the superposition of four sheets respectively assigned to the various values of g.

Figure 7B:
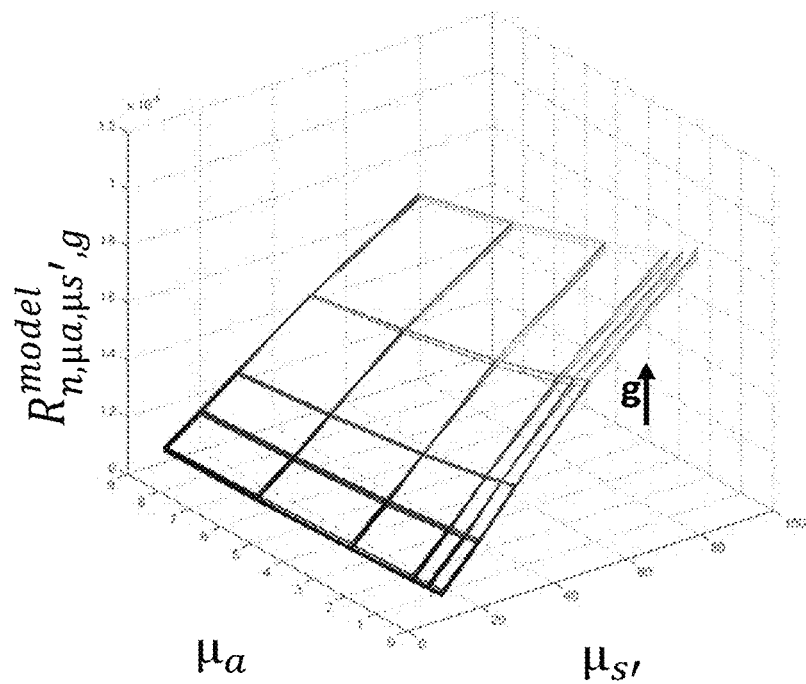
Figure 7C:
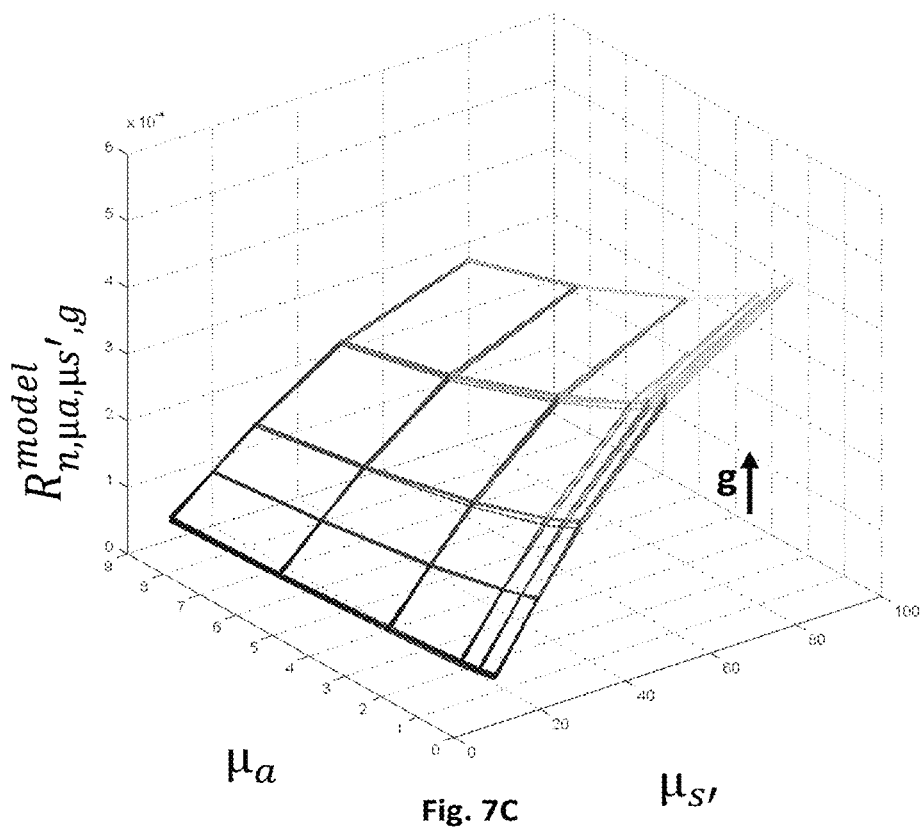
Figure 7D:
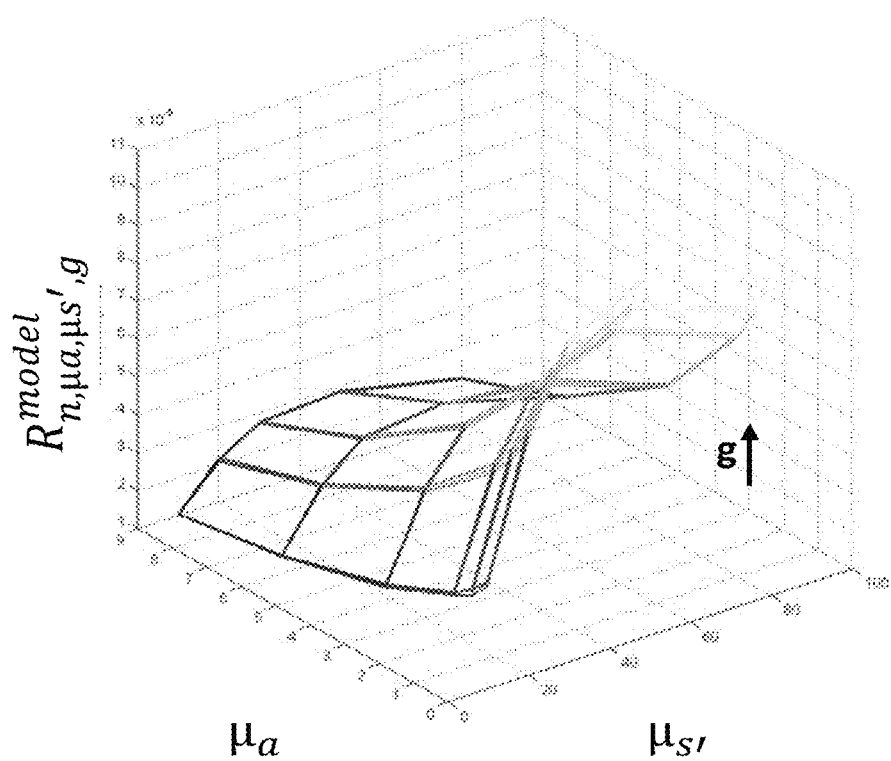

On the basis of FIG. 7D, which corresponds to a backscattering distance of greater than a few hundred μm, the influence of the value of the anisotropy coefficient g on the reflectance is small: whatever its value, the value of the reflectance, for a given pair (μa, μs'), does not evolve significantly. The scattering of the light is correctly described by the coefficients μa and μs' by means of an arbitrary determination of the anisotropy coefficient.

When the backscattering distance is small, for example less than 100 μm or 200 μm, as is the case in FIG. 7A, and, to a lesser extent, in FIGS. 7B and 7C, the reflectance evolves in a non-negligible manner as a function of the anisotropy coefficient. In FIG. 7A, which corresponds to a backscattering distance of 65 μm, the various sheets, corresponding to various values of g, are distinctly separated from one another. Hence, one and the same reflectance value can correspond to several pairs (μa, μs'), depending on the value of the anisotropy coefficient g. Thus, the taking into account of an anisotropy coefficient defined in an arbitrary manner is no longer suitable. It then becomes useful to determine it experimentally.

Stated otherwise, in the vicinity of the surface of the sample, the scattering of the photons can no longer be modelled, satisfactorily, by considering the solely absorption coefficient $\mu_a$ and the reduced scattering coefficient $\mu_s'$, but by also considering the scattering anisotropy coefficient.

According to a second example, represented in FIG. 5B, and subject to having a sufficient number of measurements at different backscattering distances $D_n$ of less than 200 μm, it is possible to determine $\mu_a$, $\mu_s'$ and g, (or $\mu_a$, $\mu_s$ and g) jointly by applying steps 110 to 150 described previously, step 160 being replaced with a step 161 in which, for at least one wavelength λ, and for a plurality of backscattering distances $D_n$, of less than 200 μm, the triplet ($\mu_a(\lambda)$, $\mu_s'(\lambda)$, g) is determined which exhibits the least disparity between the reflectance $R_n(\lambda)$ measured, at the wavelength λ, and a reflectance $R_{n,\mu a,\mu s',g}^{model}$ modelled for various values of the triplet (μa, μs', g). This determination can be carried out by minimizing a quadratic disparity, according to the expression:

$$(\mu_a(\lambda), \mu_s'(\lambda), g(\lambda)) = \mathrm{argmin}_{\mu a, \mu s', g}\left(\sum_{n=1}^{N}\left(R_{n,\mu a,\mu s',g}^{model}(\lambda,) - R_n(\lambda)\right)^2\right)$$

where:
N designates the number of distances taken into account. In the present case, N must be at least greater than 3 since three quantities have to be estimated, namely $\mu_a$, $\mu_s'$ and g.
$R_{n,\mu a,\mu s',g}^{model}$ is a modelled reflectance function, established for a backscattering distance $D_n$, and for various triplets of values $\mu_a$, $\mu_s'$ and g, during a calibration phase, as described previously.

This step 161 can be advantageously implemented iteratively, by fixing, for example alternatively, two parameters, out of the three sought, either at an arbitrary initial value or at a value determined during a previous iteration. The iterative algorithm may then converge towards a triplet of values (μa, μs', g).

The inventors have moreover produced various models, showing that when the backscattering distance is small, typically less than 1/μs', the influence of the absorption coefficient $\mu_a$ on the reflectance is small.

Profiting from these findings, there is proposed a third exemplary method, which constitutes a preferential method for determining the optical properties which is more robust than the previous method and which is represented in FIG. 5C.

It comprises steps 110 to 150 such as described above, step 120 comprising the acquisition:
of two optical backscattering signals ($52_1$, $52_2$), termed near signals, emanating respectively from the surface of the sample at two, so-called "near", backscattering distances $D_1$ and $D_2$ of less than 200 μm, or, in a more general manner, of less than 1/μs'.
of two backscattering optical signals, termed far signals ($52_3$, $52_4$), emanating respectively from the surface of the sample at two, so-called "far", backscattering distances $D_3$ and $D_4$ greater than the said near distances ($D_1$, $D_2$) and preferably greater than 200 μm, or, in a more general manner, greater than 1/μs', and more preferably greater than 500 μm.

Step 160 is replaced with a step 162, comprising:
Sub-step 162.1: the determination, for at least one wavelength λ, or for at least one spectral band, of the reduced scattering coefficient $\mu_s'(\lambda)$ and of the absorption coefficient $\mu_a(\lambda)$ by comparing the reflectances $R_3$ and $R_4$, measured at the far backscattered distances $D_3$ and $D_4$, with values of modelled reflectances $R_{3,\mu a,\mu s'}^{model}$, $R_{4,\mu a,\mu s'}^{model}$ in a manner analogous to step 160 described above. This comparison can take the form of a minimization of a quadratic disparity, according to the expression:

$$(\mu_a(\lambda), \mu_s'(\lambda)) = \mathrm{argmin}_{\mu_a(\lambda),\mu_s'(\lambda)}\left(\sum_{n=3}^{n=4}\left(R_{n,\mu a,\mu s'}^{model}(\lambda) - R_n(\lambda)\right)^2\right)$$

where $R_{n,\mu a,\mu s'}^{model}$ designates a reflectance modelled at the backscattering distance $D_n$, for a pair of values (μa, μs').
Sub-step 162.2: the determination, for the same wavelength, or the same spectral band as during the previous sub-step, of the scattering coefficient $\mu_s(\lambda)$ and of the anisotropy coefficient g, by comparing the reflectances $R_1$ and $R_2$, measured at the short distances $D_1$ and $D_2$, with values of reflectances $R_{1,\mu s,g}^{model}$ and $R_{2,\mu s,g}^{model}$, modelled by considering respectively the backscattering distances $D_1$ and $D_2$, as well as various values of $\mu_s$ and of g, in a manner analogous to step 160 described above. This comparison can take the form of a minimization of a quadratic disparity, according to the expression:

$$(\mu_s(\lambda), g) = \mathrm{argmin}_{\mu s,(\lambda),g}\left(\sum_{n=1}^{n=2}\left(R_{n,\mu s,g}^{model}(\lambda,) - R_n(\lambda)\right)^2\right)$$

where $R_{n,\mu_s,g}^{model}$ designates a reflectance modelled at the backscattering distance $D_n$, and a pair of values $(\mu_s,g)$.

This algorithm is implemented by considering the following constraint:

$$\mu_s'(\lambda)=\mu_s(\lambda)(1-g(\lambda)) \qquad (5)$$

$\mu_s'(\lambda)$ being determined during the previous step 162.1.

Moreover, determining $\mu_a$, during the first step makes it possible, during the second step, to select values of the modelled reflectance $R_{n,\mu_s,g}^{model}$ taking account of the value $\mu_a$ thus established. One sees the whole benefit of combining measurements at large and at small backscattering distance.

When the value of the absorption coefficient is known, or fixed arbitrarily, step 162.1 is aimed solely at determining $\mu_s'(\lambda)$ by taking into account the value of the said absorption coefficient. In this case, it is not necessary to have two measurements $D_3$, $D_4$ at far distances. A measurement at a single distance ($D_3$ or $D_4$) can suffice.

Moreover, one and the same backscattered signal can be used both during the first step 162.1 and during the second step 162.2. The accuracy of the measurement is then improved, in particular when the coefficient $\mu_s'$ is not homogeneous versus sample depth.

The above methods were described by considering a reflectance signal $R_n$ established, by applying a calibration function fcalib to the intensity of a backscattering signal $S_n$. In a general manner the calibration function performs a fitting of the backscattering signal $S_n$ by taking instrument parameters into account, in particular noise, effectiveness, and optionally a normalization by the intensity of the incident beam.

When the detector is provided with a spectrometric function, the methods described above can be implemented for a plurality of different wavelengths or spectral bands. In this case, the various optical properties are obtained as a function of the wavelength or of the spectral band considered.

The invention claimed is:

1. A method for determining an optical property of a sample, comprising:
    illuminating a surface of the sample with a light beam, to form, on said surface, an elementary illumination zone, corresponding to the part of the surface illuminated on the sample;
    detecting N optical signals, backscattered by the sample, each optical signal emanating from the surface of the sample, at a level of an elementary detection zone, at a backscattering distance from the said elementary illumination zone, N being an integer greater than or equal to 1, to form detected signals, each elementary detection zone being separated from the elementary illumination zone;
    determining at least one optical property of the sample, by a comparison between:
        a function of each optical signal thus detected; and
        a plurality of estimations of the function, each estimation being carried out by considering a predetermined value of the optical property,
    the determining characterizing a superficial layer of the sample, the superficial layer extending from the illuminated surface,
    wherein at least one backscattering distance, separating an elementary detection zone from the elementary illumination zone, is less than 200 μm, and
    wherein the optical property comprises at least one of:
        a light scattering anisotropy factor, representing a mean angle of light scattering;
        a light absorption coefficient;
        a light scattering coefficient; and
        a reduced light scattering coefficient.

2. The method according to claim 1, wherein the at least one backscattering distance is less than 150 μm.

3. The method according to claim 1, wherein the at least one backscattering distance includes at least two backscattering distances that are less than 200 μm.

4. The method according to claim 1, further comprising:
    detecting at least two optical signals emanating from the surface of the sample:
        a near backscattered signal emitted at a near backscattering distance of less than 200 μm;
        a far backscattered signal emitted at a far backscattering distance of greater than the near distance;
    determining a first optical property on a basis of the near backscattered signal; and
    determining a second optical property, different from the first optical property, on a basis of the far backscattered signal.

5. The method according to claim 4, further comprising:
    detecting at least two near backscattered optical signals emanating from the surface of the sample at two different backscattering distances, the two distances being less than 200 μm;
    determining a reduced scattering coefficient from the far backscattered optical signal;
    determining a scattering coefficient and a scattering anisotropy factor from the two near backscattered optical signals, as well as from the determined reduced scattering coefficient.

6. The method according to claim 5, further comprising:
    detecting at least two far backscattered optical signals, emanating from the surface of the sample at two different backscattering distances, the at least two far backscattering distances being greater than 200 μm,
    determining an absorption coefficient from the at least two far backscattered optical signals.

7. The method according to claim 1, wherein the sample examined is the skin of a human or of an animal.

8. The method according to claim 7, further comprising:
    based on the determined at least one optical property, estimating parameters of the skin including a concentration of chromophores.

9. The method according to claim 1, wherein the backscattered optical signal is measured at a plurality of wavelengths.

10. The method according to claim 1, wherein the function of each detected signal is a reflectance function, representing an intensity of the detected signal, corresponding to a backscattering distance, relative to an intensity of the light beam.

* * * * *